(12) United States Patent
Riis et al.

(10) Patent No.: US 11,224,745 B2
(45) Date of Patent: Jan. 18, 2022

(54) SELF-POWERED ELECTRODE ARRAY

(71) Applicant: Oticon Medical A/S, Smørum (DK)

(72) Inventors: Søren Kamaric Riis, Smørum (DK); Guillaume Tourrel, Vallauris (FR); Bradford Backus, Vallauris (FR)

(73) Assignee: OTICON MEDICAL A/S, Smørum (DK)

( * ) Notice: Subject to any disclaimer, the term of this patent is extended or adjusted under 35 U.S.C. 154(b) by 139 days.

(21) Appl. No.: 16/654,109

(22) Filed: Oct. 16, 2019

(65) Prior Publication Data

US 2020/0121920 A1 Apr. 23, 2020

(30) Foreign Application Priority Data

Oct. 17, 2018 (EP) ..................................... 18200860

(51) Int. Cl.
*A61N 1/36* (2006.01)
*A61N 1/05* (2006.01)
(Continued)

(52) U.S. Cl.
CPC ....... *A61N 1/36038* (2017.08); *A61N 1/0541* (2013.01); *A61N 1/36036* (2017.08);
(Continued)

(58) Field of Classification Search
CPC ............ A61N 1/36038; A61N 1/36036; A61N 1/0541; A61N 1/3756; A61N 1/3785;
(Continued)

(56) References Cited

U.S. PATENT DOCUMENTS 9,884,180 B1    2/2018  Ho et al.
10,112,046 B1 * 10/2018  Downs, Jr. ........... A61N 1/0541
(Continued)

FOREIGN PATENT DOCUMENTS

CN     105854183 B    4/2018
EP     2 853 289 A1   4/2015
(Continued)

OTHER PUBLICATIONS

Asadnia et al., "From Biological Cilia to Artificial Flow Sensors: Biomimetic Soft Polymer Nanosensors with High Sensing Performance", Scientific Reports, Dec. 1, 2016, XP055571000, vol. 6, No. 1, Total 13 pages.
(Continued)

*Primary Examiner* — Catherine M Voorhees
(74) *Attorney, Agent, or Firm* — Birch, Stewart, Kolasch & Birch, LLP

(57) ABSTRACT

A cochlear implant device is disclosed, comprising an inductive antenna, a stimulation unit, an electrode array, and an energy harvesting apparatus. The inductive antenna is configured to receive energy to operate the cochlear implant and to receive signals for a stimulation of a cochlea via an electrode array comprising a plurality of electrodes. The stimulation unit is configured to process the signals received by the inductive antenna to be usable for the electrodes of the electrode array. The electrode array is configured to apply the signals processed by the stimulation unit to the cochlea for the stimulation thereof. The energy harvesting apparatus is connected to the stimulation unit or to the electrode array, and is configured to harvest energy based on at least one of thermal, biochemical, biophysical, and mechanical processes/phenomena pertaining to the cochlea, and is configured to provide harvested energy to the stimulation unit or the electrode array, respectively.

11 Claims, 10 Drawing Sheets

(51) Int. Cl.
 *A61N 1/378* (2006.01)
 *A61N 1/375* (2006.01)
 *H01L 41/113* (2006.01)

(52) U.S. Cl.
 CPC ......... *A61N 1/3756* (2013.01); *A61N 1/3785* (2013.01); *H01L 41/113* (2013.01)

(58) Field of Classification Search
 CPC ........................ A61N 1/3787; A61N 1/37229; H01L 41/113; H02N 2/185
 See application file for complete search history.

(56) References Cited

U.S. PATENT DOCUMENTS

| | | | |
|---|---|---|---|
| 2010/0234793 A1* | 9/2010 | Dacey, Jr. .......... | A61B 5/14546 604/8 |
| 2013/0238073 A1 | 9/2013 | Makdissi et al. | |
| 2014/0247020 A1* | 9/2014 | Stankovic ................ | A61F 2/10 320/166 |
| 2015/0088226 A1* | 3/2015 | Tourrel .............. | A61N 1/36038 607/57 |
| 2015/0091415 A1 | 4/2015 | Deterre et al. | |
| 2015/0231394 A1* | 8/2015 | Knisely .............. | A61N 1/36038 607/57 |
| 2018/0071532 A1* | 3/2018 | Carter ................... | A61N 1/0541 |
| 2018/0133487 A1* | 5/2018 | Shah .................... | A61N 1/3754 |

FOREIGN PATENT DOCUMENTS

| | | |
|---|---|---|
| WO | WO 2006/017226 A1 | 2/2006 |
| WO | WO 2007/109272 A2 | 9/2007 |
| WO | WO 2007/109272 A3 | 9/2007 |

OTHER PUBLICATIONS

Shi et al., "MEMS Based Broadband Piezoelectric Ultrasonic Energy Harvester (PUEH) for Enabling Self-Powered Implantable Biomedical Devices", Scientific Reports, Apr. 26, 2016, XP055571005, vol. 6, No. 1, Total 10 pages.

* cited by examiner

SELF-POWERED ELECTRODE ARRAY

FIELD

The present disclosure relates to a self-powered electrode array. More particularly, the disclosure relates to a hearing device having a self-powered electrode array, which comprises an energy harvester for providing energy to the hearing device.

BACKGROUND

Today, commercial cochlear implants are all powered by a non implantable energy source, that is, external energy sources. Such an energy source is typically provided by a speech processor having a behind-the-ear (BTE) or a "button processor" form factor. The battery is typically a non-rechargeable Air zinc battery or a rechargeable Lithium Ion battery.

The energy is transferred to the cochlear implant via an inductive link which is established by coupling two coils together: one coil, which is external to the body, is coupled to another coil, which is integrated in the implantable device (the cochlear implant). However, the yield of energy transfer (the energy transfer efficiency) is typically only about 25%.

For a user (patient), a constraint is to manage the battery and to be sure to have enough power for the implant. Further, the battery has to be changed or recharged from time to time.

Furthermore, due to the inductive coils being large, the use of a cochlear implant generates an aesthetic issue for the user.

Therefore, there is a need to provide a solution that addresses at least some of the above-mentioned problems.

SUMMARY

According to an aspect, a cochlear implant device is provided, comprising an inductive antenna, a stimulation unit, an electrode array, and an energy harvesting apparatus. The inductive antenna is configured to receive energy to operate the cochlear implant and to receive signals for a stimulation of a cochlea via an electrode array comprising a plurality of electrodes. The stimulation unit is configured to process the signals received by the inductive antenna to be usable for the electrodes of the electrode array. The electrode array is configured to apply the signals processed by the stimulation unit to the cochlea for the stimulation thereof. The energy harvesting apparatus is connected to the stimulation unit or to the electrode array, and is configured to harvest energy based on at least one of thermal, biochemical, biophysical, and mechanical processes or phenomena pertaining to the cochlea, and is configured to provide harvested energy to the stimulation unit or the electrode array, respectively.

This allows for providing a solution to the above-mentioned problem of the invention. Further, this allows reducing the overall energy consumption of the cochlear implant since energy is provided by the harvesting unit and hence, only a part of the energy consumed by the cochlear implant needs to be provided an external energy source. Even further, this allows reducing the size of the inductive antenna and hence allows improving the aesthetic appearance for the user.

Preferably, a device according to any of the disclosed aspects is provided, wherein the energy harvesting apparatus is attached and electrically connected to the electrode array.

This allows delivering the energy to the electrode array. Furthermore, a distance between the harvesting apparatus and the electrode array is reduced, so that an electrical loss can be reduced.

Preferably, a device according to any of the disclosed aspects is provided, wherein the energy harvesting apparatus is based on an actuator made from a piezoelectric material.

This allows for providing an efficient energy harvesting apparatus based on a piezoelectric effect.

Preferably, a device according to any of the disclosed aspects is provided, wherein the electrode array with the energy harvesting apparatus is designed to be insertable into the scala tympani of the cochlea.

This allows for providing a small energy harvesting apparatus, which can be inserted into the cochlea. Furthermore, electrical losses can be reduced due to a small arrangement.

Preferably, a device according to any of the disclosed aspects is provided, wherein the harvested energy is mechanical energy harvested from movement of the cochlea liquid.

This allows for making use of the movement of the cochlear liquid, which is moved by acoustic sound or movements of the head.

Preferably, a device according to any of the disclosed aspects is provided, wherein the energy harvesting apparatus is configured to harvest the mechanical energy from the movement of the cochlear liquid by using a harvesting unit having a hair shape configured to generate an electrical potential under the influence of movement of the cochlear liquid.

This allows for providing a small energy harvesting apparatus, which can be introduced into the cochlea, while the electrical potentials can be used to provide energy to the cochlear implant.

Preferably, a device according to any of the disclosed aspects is provided, wherein the energy harvesting apparatus is based on harvesting energy from a heat difference in the human body.

This allows for providing a harvesting unit employing a heat difference in the human body, which allows providing a more flexible solution for an energy harvesting apparatus.

Preferably, a device according to any of the disclosed aspects is provided, further comprising an energy storage apparatus connected to the energy harvesting apparatus and configured to be charged by the energy harvesting apparatus.

This allows for storing the generated electrical energy, so that the overall energy consumption can be reduced. Furthermore, electrical energy generated in times, where a lot of energy can be generated, can be stored for use in times, where only little motion is present.

Preferably, a device according to any of the disclosed aspects is provided, wherein the energy harvesting apparatus additionally comprises a rectifying means for rectifying the voltage generated by the energy harvesting apparatus for charging of the energy storage apparatus.

This allows for making use of oscillatory movements and allows to rectify an oscillating voltage into a direct current for use with the cochlear implant.

Preferably, a device according to any of the disclosed aspects is provided, wherein the energy storage apparatus is further configured to be additionally charged by energy received by the inductive antenna, and the inductive antenna is further configured to receive energy for supplying energy to the energy storage apparatus.

This allows for charging the energy storage apparatus with energy provided externally, so that it is also possible to operate the cochlear implant by energy stored in the energy storage apparatus, and hence, to use the cochlear implant for a certain time without the inductive link. This allows an improvement of the aesthetic appearance for the user.

Preferably, a device according to any of the disclosed aspects is provided, wherein each electrode of the electrode array is provided with a switching means configured to apply the energy stored in the energy storage apparatus to the respective electrode in accordance with the received electrical stimulation signals from the stimulation unit.

This allows for saving energy of the cochlear implant, since the energy provided by the energy storage apparatus can be directly used for the electrodes.

Preferably, a device according to any of the disclosed aspects is provided, wherein the switching means is configured to provide an electrical amplification of the electrical stimulation signals.

This allows for reducing the signal level of the signals transmitted from the stimulation unit to any of the electrodes, and to switch a voltage coming from energy storage apparatus for use with the electrode.

Preferably, a device according to any of the disclosed aspects is provided, wherein the energy storage apparatus comprises a capacitor connected to the energy harvesting apparatus and connected to the switching means.

This allows for providing a compact energy storage apparatus by providing a capacitor, while also providing a possibility for storing energy.

Preferably, a device according to any of the disclosed aspects is provided, wherein the inductive antenna is further configured to transmit information relating to the cochlear implant.

This allows for providing a feedback channel from the cochlear implant, so that the user can receive information about the status of the cochlear implant, such as the storage state of the energy storage apparatus, a current energy consumption, and the like.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

DETAILED DESCRIPTION

Figure 1A:
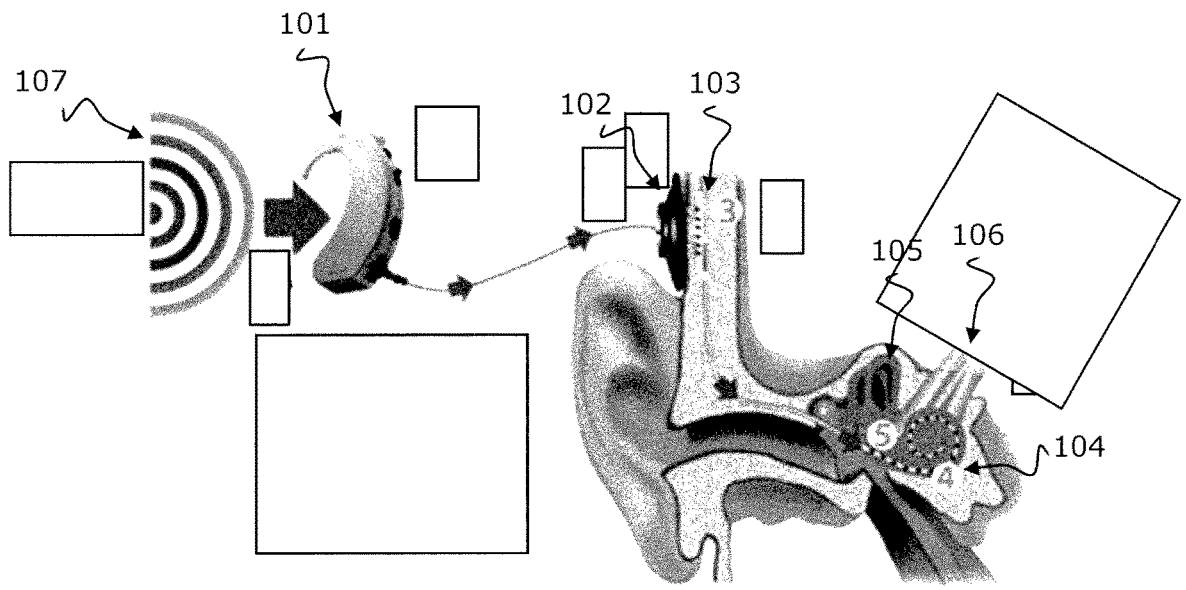
FIG. 1A illustrates a cochlear implant hearing aid system in the prior art.

The detailed description set forth below in connection with the appended drawings is intended as a description of various configurations. The detailed description includes specific details for the purpose of providing a thorough understanding of various concepts. However, it will be apparent to those skilled in the art that these concepts may be practised without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout this disclosure. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

A hearing device may include a hearing aid that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. The "hearing device" may further refer to a device such as an earphone or a headset adapted to receive an audio signal electronically, possibly modifying the audio signal and providing the possibly modified audio signals as an audible signal to at least one of the user's ears. Such audible signals may be provided in the form of an acoustic signal radiated into the user's outer ear, or an acoustic signal transferred as mechanical vibrations to the user's inner ears through bone structure of the user's head and/or through parts of middle ear of the user or electric signals transferred directly or indirectly to cochlear nerve and/or to auditory cortex of the user.

The hearing device is adapted to be worn in any known way. This may include i) arranging a unit of the hearing device behind the ear with a tube leading air-borne acoustic signals into the ear canal or with a receiver/loudspeaker arranged close to or in the ear canal such as in a Behind-the-Ear type hearing aid, and/or ii) arranging the hearing device entirely or partly in the pinna and/or in the ear canal of the user such as in a In-the-Ear type hearing aid or In-the-Canal/Completely-in-Canal type hearing aid, or iii) arranging a unit of the hearing device attached to a fixture implanted into the skull bone such as in Bone Anchored Hearing Aid or Cochlear Implant, or iv) arranging a unit of the hearing device as an entirely or partly implanted unit such as in Bone Anchored Hearing Aid or Cochlear Implant.

A "hearing system" refers to a system comprising one or two hearing devices, and a "binaural hearing system" refers to a system comprising two hearing devices where the devices are adapted to cooperatively provide audible signals to both of the user's ears. The hearing system or binaural hearing system may further include auxiliary device(s) that communicates with at least one hearing device, the auxiliary device affecting the operation of the hearing devices and/or benefitting from the functioning of the hearing devices. A wired or wireless communication link between the at least one hearing device and the auxiliary device is established that allows for exchanging information (e.g. control and status signals, possibly audio signals) between the at least one hearing device and the auxiliary device. Such auxiliary devices may include at least one of remote controls, remote microphones, audio gateway devices, mobile phones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing device. The remote control is adapted to control functionality and operation of the at least one hearing devices. The function of the remote control may be implemented in a SmartPhone or other electronic device, the SmartPhone/electronic device possibly running an application that controls functionality of the at least one hearing device.

In general, a hearing device includes i) an input unit such as a microphone for receiving an acoustic signal from a user's surroundings and providing a corresponding input audio signal, and/or ii) a receiving unit for electronically receiving an input audio signal. The hearing device further includes a signal processing unit for processing the input audio signal and an output unit for providing an audible signal to the user in dependence on the processed audio signal.

The input unit may include multiple input microphones, e.g. for providing direction-dependent audio signal processing. Such directional microphone system is adapted to enhance a target acoustic source among a multitude of acoustic sources in the user's environment. In one aspect, the directional system is adapted to detect (such as adaptively detect) from which direction a particular part of the microphone signal originates. This may be achieved by using conventionally known methods. The signal processing unit may include amplifier that is adapted to apply a frequency dependent gain to the input audio signal. The signal processing unit may further be adapted to provide other relevant functionality such as compression, noise reduction, etc. The output unit may include an output transducer such as a loudspeaker/receiver for providing an air-borne acoustic signal transcutaneously or percutaneously to the skull bone or a vibrator for providing a structure-borne or liquid-borne acoustic signal. In some hearing devices, the output unit may include one or more output electrodes for providing the electric signals such as in a Cochlear Implant.

In a research context, some manufacturers of cochlear implants have studied a fully implantable device comprising an implantable housing with a stimulation unit and a battery, connected to an implantable microphone and an electrode array. Researchers expect in the future to reach an energy consumption of a cochlear implant to be below the 1 mW. One of the strengths of such an implant architecture is to have energy directly available, and so to be able to avoid the inductive link for the typical use case, the stimulation workflow. The inductive link is in this case only needed for recharging of the battery.

In such a case, a rechargeable battery needs to be replaced approximately every 8 years on average. However, a surgical operation is needed for a replacement of the battery, which is an issue for user, and provides additional risks for the health of the user.

As described above, current cochlear implants and fully implantable devices still need a power source. A replacement of such a power source is needed more frequently for the non-implantable devices currently used in commercial solutions, or may be less frequent for an implantable device having a battery in the full implantable device.

The invention proposes to generate electrical energy close to the stimulation site and to use it in the implantable device directly, and consequently to limit or completely suppress energy needed in the implantable device, at least for the stimulation and the energy provided to the user.

Furthermore, the invention describes a concept of a multi-channel self-powered electrode array. The electrode array is composed of several autonomous elements comprising an energy harvesting cell based on an artificial hair bundles, and stimulating electrode contact and a connection between them.

Now referring to FIG. 1A, a cochlear implant hearing aid system of the prior art is illustrated having a sound processor 101, an external antenna 102, an implant, and an electrode array 104 implanted into the cochlea 105.

Acoustic signals 107, such as speech or the like, are detected by a microphone implemented in the sound processor 101, and are converted in the sound processor 101 into signals, which are usable in the cochlear implant. Using the external antenna 102, the signals usable in the cochlear implant are transmitted to the implanted coil 103 of the cochlear implant below the skin of the user. The received signals are transmitted to the electrode array 104, which stimulates the cochlea 105 accordingly, so that a hearing impression is generated which is transmitted to the brain of the user by the auditory nerve 106.

Furthermore, in the prior art, a battery is included in the sound processor 101, and energy from the battery is transmitted via the inductive link provided by the external antenna 102 and the implanted coil 103 to the cochlear implant.

Figure 1B:
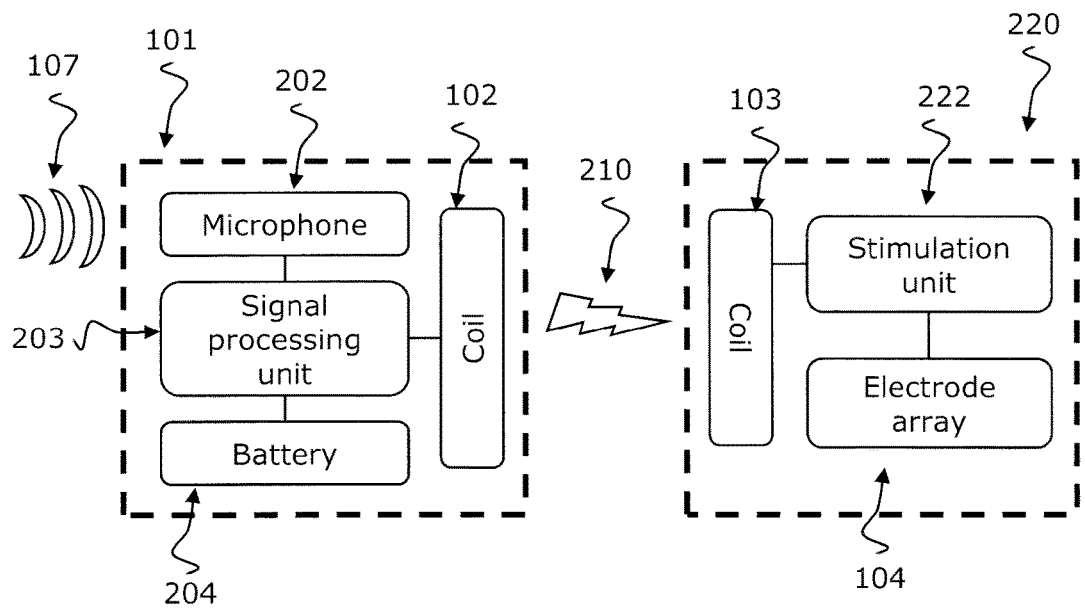
FIG. 1B illustrates a schematic diagram illustrating an overview over a cochlear implant hearing aid system.

FIG. 1B illustrates a schematic diagram illustrating an overview over a cochlear implant hearing aid system of the prior art. The sound processor 101 (indicated by the dashed lines) comprises a microphone 202, a signal processing unit 203, and a battery 204. Furthermore, the coil 102 is an integral part to the sound processor 101, even though it is configured to be placed on the head of the user.

The coil 102 generates an inductive field 210, which is modulated by the signals, and which provides an electromagnetic field strength for transferring energy from the battery 204 to the cochlear implant.

The signals and the energy of the inductive field 210 are received by the coil 103 of the cochlear implant 220. The stimulation unit 222 receives the signals and forwards them to the electrode array 104. The energy is provided to operate the stimulation unit 222.

Figure 1C:
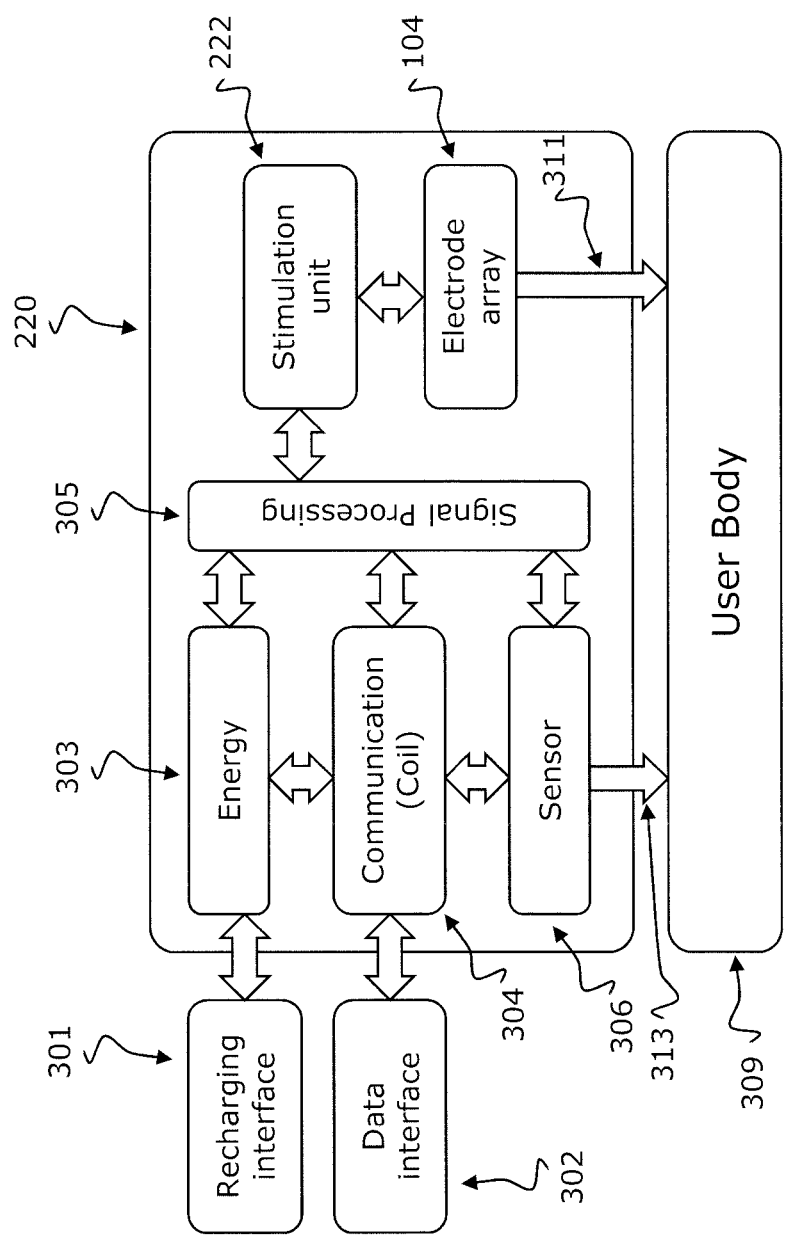
FIG. 1C illustrates a block diagram for illustrating energy and signal flow in a hearing aid device in the prior art.

FIG. 1C illustrates a modular architecture of electronics inside the cochlear implant 220 by illustrating logical connections between components of the cochlear implant 220. The coil 103 as shown in FIG. 1A and FIG. 1B provides the recharging interface 301 and the data interface 302, for providing energy 303 and communication 304 to the signal processing unit 305. The cochlear implant 220 may further provide a sensor 306 providing additional information for the signal processing unit 305. The signal processing unit 305 provides signal to the stimulation electronics 222, which operates the electrode array 104. The electrode array 104 provides (311) stimulation to the cochlea in the body 309 of the user, while the sensor 306 senses (313) parameters such as temperature or the like of the user's body 309.

Figure 2A:
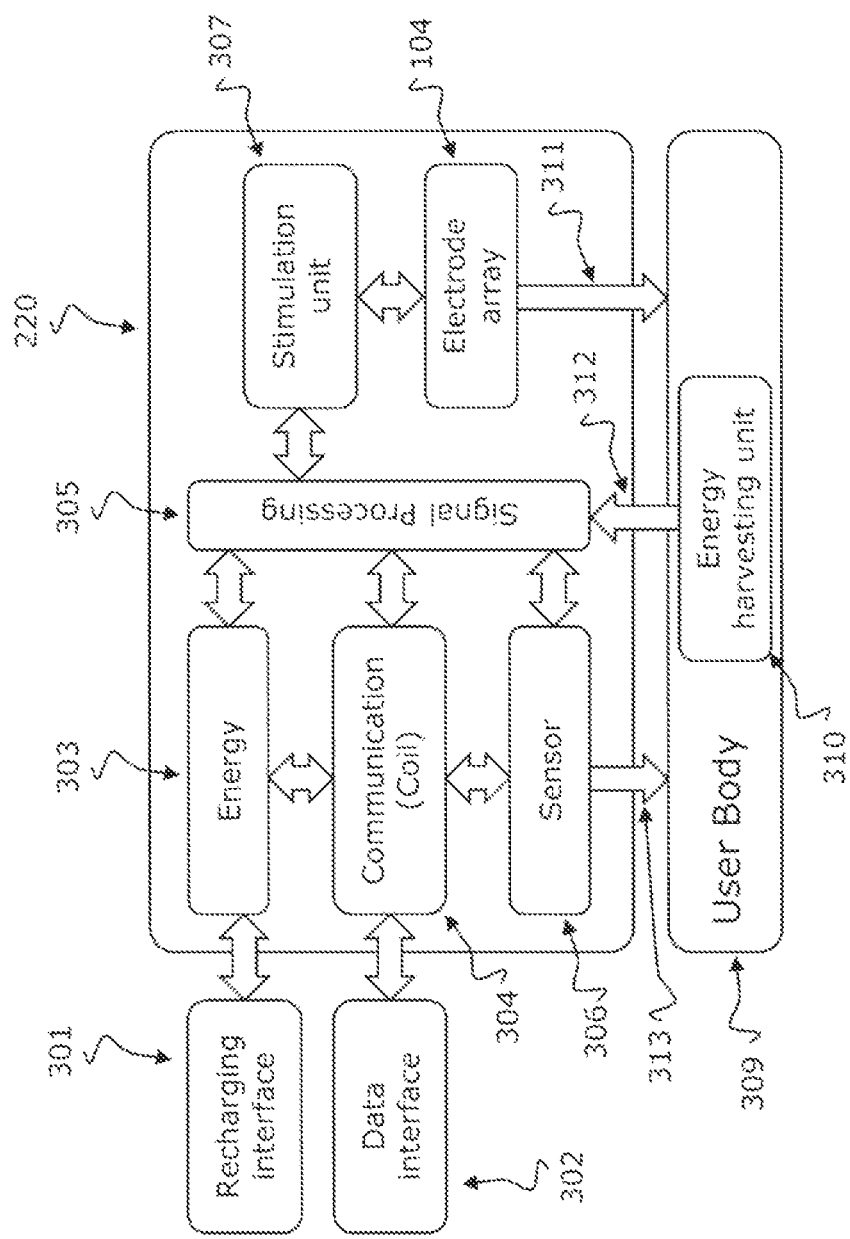
FIG. 2A illustrates a block diagram for illustrating energy and signal flow in a device according to an embodiment of the disclosure.

FIG. 2A illustrates an architecture according to various embodiments of the invention. Additionally, to the cochlear implant 220, an energy harvesting apparatus 310 is provided in the body of the user, which provides (312) energy to the cochlear implant. It is noted that the same numerals are used for same or similar components and detailed description thereof is omitted.

In other words, a cochlear implant device comprises an inductive antenna 103, a stimulation unit 222, an electrode array 104, and an energy harvesting apparatus 310. The inductive antenna 103 is configured to receive energy to operate the cochlear implant 220 and to receive signals for a stimulation of a cochlea 103 via an electrode array 104 comprising a plurality of electrodes. The stimulation unit 222 is configured to process the signals received by the inductive antenna 103 to be usable for the electrodes of the electrode array 104. The electrode array 104 is configured to apply the signals processed by the stimulation unit 222 to the cochlea 105 for the stimulation thereof. The energy harvesting apparatus 310 is connected to the stimulation unit 222 or to the electrode array 104, and is configured to harvest energy based on at least one of thermal, biochemical, biophysical, and mechanical processes or phenomena pertaining to the cochlea 105, and is configured to provide harvested energy to the stimulation unit 222 or the electrode array 104, respectively.

According to various embodiments, the energy harvesting apparatus 310 is configured to generate electric energy from an energy source within the human body, and converts the electric energy into a voltage, which is usable by the electrode area or by the cochlear implant.

According to various embodiments, the inductive antenna 103 may additionally be configured to transmit information relating to the cochlear implant.

According to various embodiments, the energy harvesting apparatus 310 may be attached and electrically connected to the electrode array 104.

In the example shown in FIG. 2A, the energy harvesting apparatus 310 is configured to be able to deliver energy for the stimulation of the cochlea 105, but is also configured to harvest energy e.g. from the cochlea 105. However, the energy harvesting apparatus 310 may be configured to harvest energy from another source of energy in the human body. The energy harvesting apparatus 310 may be provided connected to the electrode array 104, or may be provided as a separate unit.

Other possibilities to harvest energy from a human body, which may be employed according to various embodiments as sources of energy to supply electrical power to a cochlear implant 220 may be sources of mechanical energy, such as vibrations, such as movements of the ear drum or the basilar membrane, the mechanical motion of the heart, or motions of the head or the whole body, such as walking or the like. Electrical energy may be generated by a bending of an actuator due to the movement, by a bending of an actuator due to external forces or accelerations, or by movement of two interacting magnetic parts, such as a magnet and a coil, and employing a variation in magnetic field strength due to movements or vibrations.

Furthermore, according to various embodiments, thermal energy can be employed, e.g. from a thermoelectric voltage (Seebeck effect) using e.g. a thin-film technology sensors or the like. For example, outer parts of the human body are mostly colder than inner parts, so that this temperature difference can be employed.

In addition, according to various embodiments, it is also possible to employ chemical potentials within the human body, such as an endolymph potential, or by using chemical compounds, such as glucose, which may be taken from blood.

According to various embodiments, also electromagnetic energy may be employed by making use of a variation of an external magnetic field or by employing electromagnetic fields using a broadband sensor on flexible technology.

According to various embodiments, the energy harvesting apparatus may additionally employ not only one source of energy, but may employ two or more sources of energy.

Since the electrode array 104 is according to various embodiments typically inserted in the scala tympani of the cochlea 105, the harvested energy may e.g. be mechanical energy generated by a vibration of the cochlea liquid. However the invention is not limited to this, and other sources of energy may be used to generate electrical energy, e.g. electrical energy may be generated from temperature differences within the human body of the user.

In other words, the electrode array 104 may be designed to be insertable into the scala tympani of the cochlea 105 together with the energy harvesting apparatus 310. However, the energy harvesting apparatus 310 may be provided at another place, e.g. implanted at the rear side of the head of the user for employing a temperature difference between the inner head and the outer surface of the head of the user.

In other words, according to various embodiments, the energy harvesting apparatus 310 may be based on harvesting energy from a heat difference in the human body.

According to various embodiments, the electrode design of the electrode array 104 does not have to be such that a bi-directional communication is possible, but can be designed so that the stimulation unit 222 sends the required stimulation information to a "self-powered cell", that is, the electrode array having an energy harvesting apparatus attached to it. In this case, the self-powered cells can manage the information being sent from the stimulation unit and can stimulate the cochlea 105 with the power harvested by the energy harvesting apparatus.

For example, the energy harvesting apparatus 310 may be based on an actuator made from a piezoelectric material. Furthermore, the energy harvesting apparatus 310 may be provided comprising several energy harvesting units may be provided, or the energy harvesting apparatus 310 may be provided having only a single energy harvesting unit. In addition, an energy harvesting apparatus 310 may be configured such that one minute energy harvesting unit is provided for each electrode of the electrode array.

It is important to balance the harvested energy in the cochlea 105 and the energy required for stimulation. However, it is expected that the harvested energy is sufficient to operate the electrode array 104. If the energy is not sufficient to operate the electrode array 104, according to various embodiments, a small amount of energy has to be sent from the stimulation unit 222 to the electrode array 104 to complete the required energy. However, also in this case, the overall energy consumption of the cochlear implant can be reduced by the energy harvesting apparatus, so that the energy transfer by the inductive link between the external coil 102 and the coil of the cochlear implant 103 can be reduced. hence, the coils can be reduced in size and the aesthetic appearance of the cochlear implant system including the cochlear implant 220 and the sound processor unit 101 having the external coil 102 can be improved.

Figure 2B:
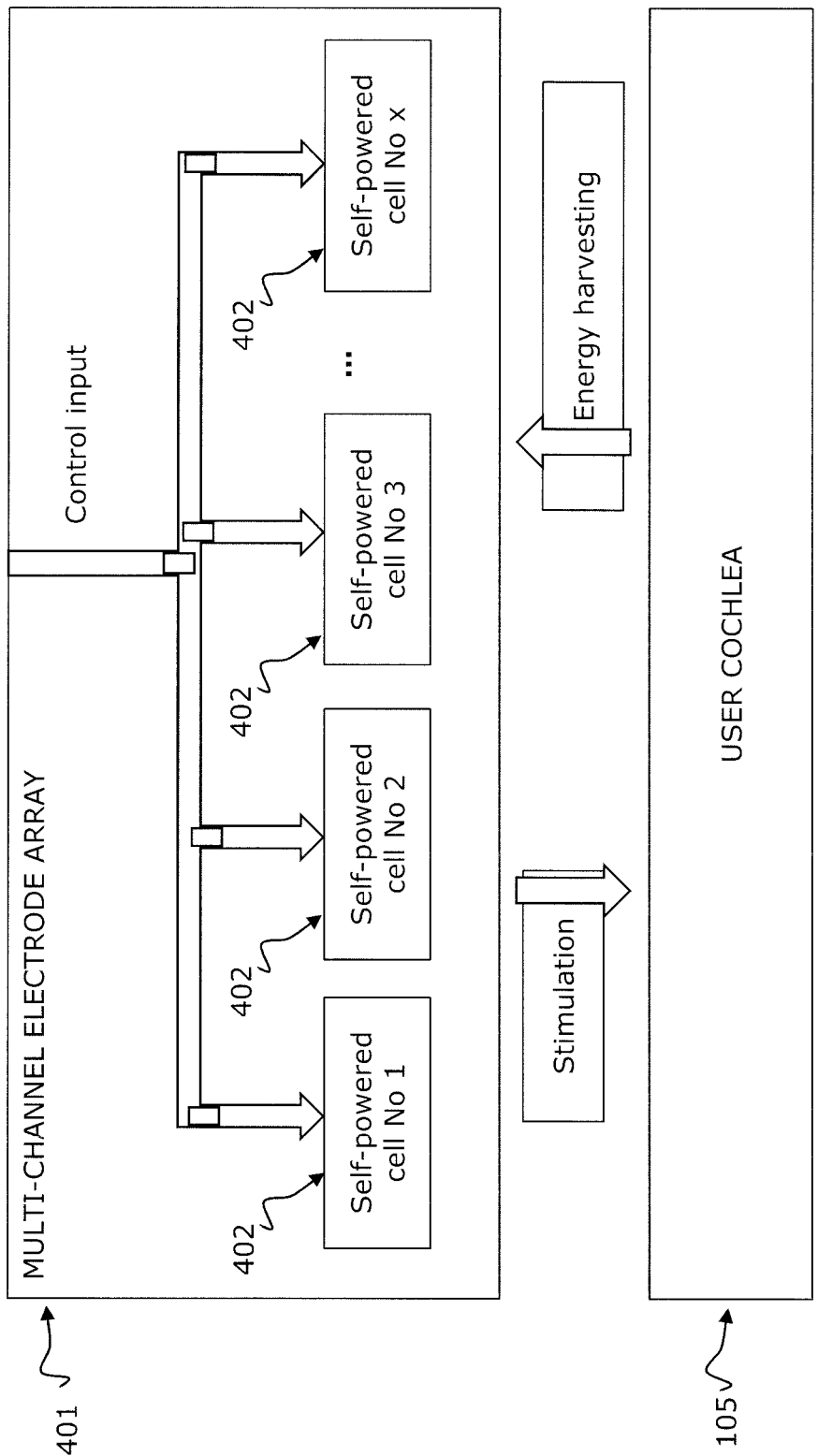
FIG. 2B illustrates a block diagram for illustrating energy and signal flow in a multi-channel electrode array according to an embodiment of the disclosure.

With reference to FIG. 2B, a configuration according to various embodiments is described, in which an energy harvesting apparatus 310 is provided having several energy harvesting units. A multi-channel electrode array 401 may be provided having several self-powered cells 402. Each self-powered cell 402 comprises an electrode for stimulation of the user cochlea, while also each self-powered cell comprises an energy harvesting unit. Energy generated by each of the energy harvesting units may be directly used in the respective self-powered cell 402, so that the energy consumption of the multichannel electrode area can be reduced.

According to various embodiments, the electrode array may be composed of a number of independent channels, which may be controlled by the stimulation unit 307. The control input from the stimulation unit 307 may be guided to each one of the self powered cells. In FIG. 2B, only four self powered cells are shown, while the number of self powered cells is not restricted. According to various embodiments, the number of self-powered cells 402 typically is determined by the frequency resolution intended to be achieved for the cochlear implant.

According to various embodiments, the multichannel electrode array 401 can be introduced into the cochlea 105 of the user, and can be configured so that the harvested energy is mechanical energy harvested from movements of the cochlea liquid. For example, according to various embodiments, the energy harvesting apparatus 310 can be configured to harvest mechanical energy from the movement of the cochlear liquid by using a harvesting unit having a hair shape configured to generate an electrical potential under the influence of movement of the cochlear liquid.

Figure 2C:
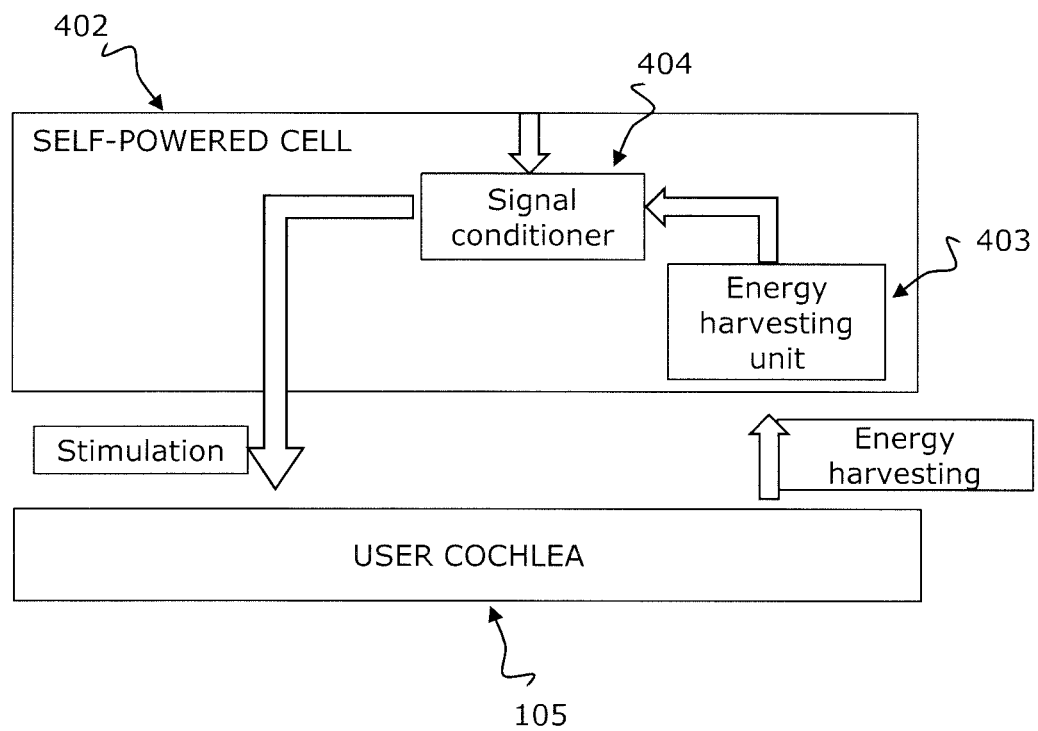
FIG. 2C illustrates a block diagram for illustrating energy and signal flow in a self-powered cell according to an embodiment of the disclosure.

FIG. 2C shows a detailed view on one example of a self powered cell according to various embodiments, which comprises a signal conditioner 404 for conditioning the signals (control input) provided by the stimulation unit 222, and an energy harvesting unit 403 for harvesting energy from the cochlea 105 of the user. Further, the conditioned signals are provided for stimulation of the cochlea 105 of the user. That is, the signal conditioner 404 translates from the signals coming from the stimulation unit 222 into the electrical signals, which are send to the electrode array 104.

Furthermore, according to various embodiments the signal conditioner 404 may be configured to reach an energy balance between the energy harvested by the energy harvesting unit and the stimulation of the cochlea 105, while it is also configured to condition the signals received by the stimulation unit 222 in order to set a stimulation threshold. This threshold may be set externally, while the respective settings may be stored in the signal processing unit 305.

That is, each of the self-powered cell may be connected to one electrode. As the harvested energy with such cells is likely to be low, one harvesting cell may be required per electrode.

However according to various embodiments, only one single harvesting apparatus 310 and only one global energy storage unit (a central energy storing means, e.g. a capacitor) may be provided, so that energy from the central energy storage apparatus may be directed to places, where it is needed within the cochlea implant. Hence, the one single energy harvesting apparatus may be provided, which is shared between the electrode cells, so that the one single harvesting cell is provided to power all the electrodes.

Figure 2D:
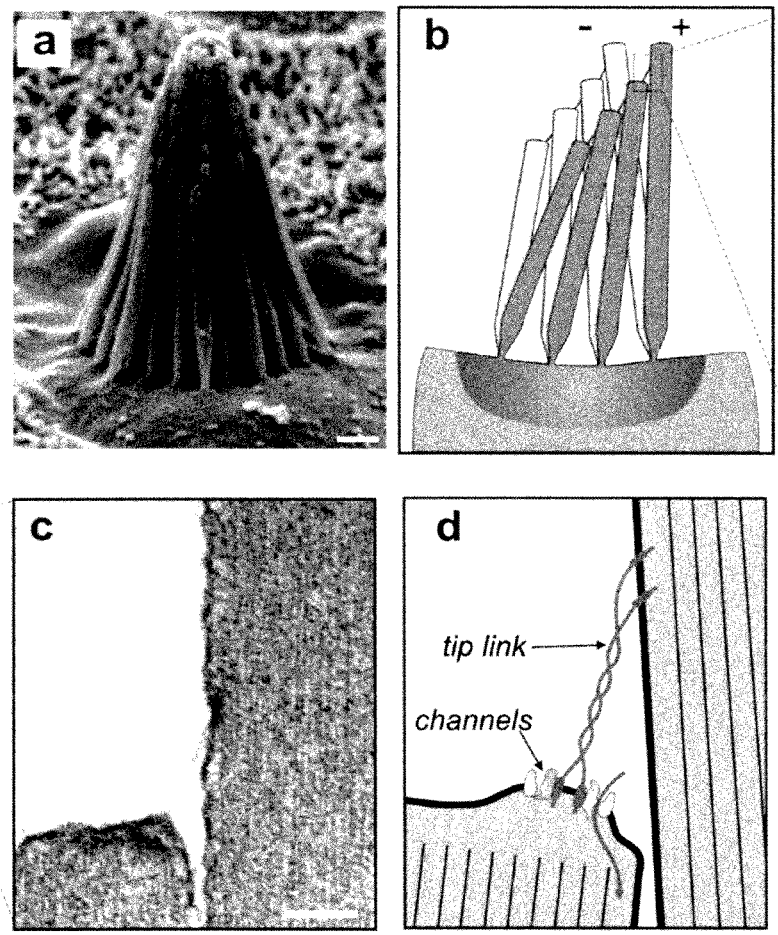
FIG. 2D shows micrographs and schematic diagrams for explaining principles of energy harvesting in an ear of a bullfrog.
Figure 2E:
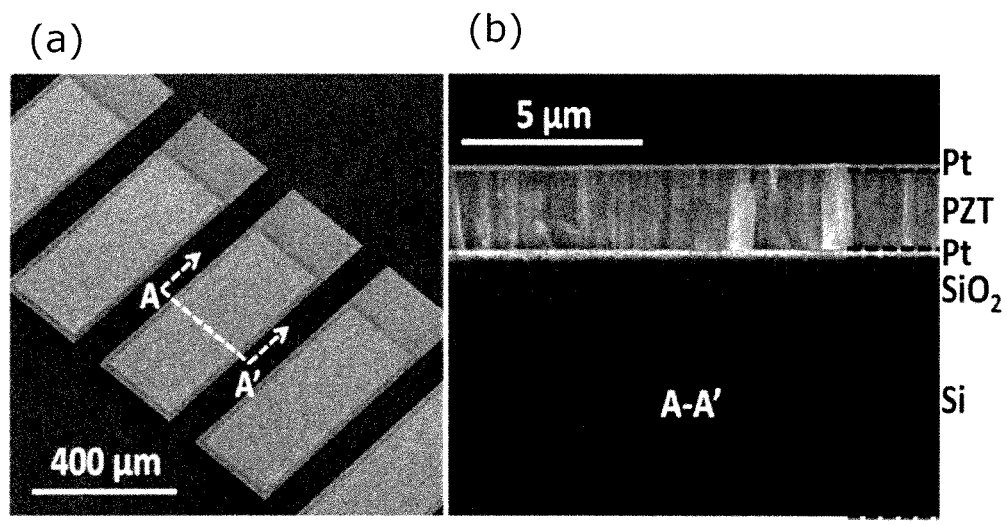
FIG. 2E illustrates micrographs of an example of a PZT diaphragm array.

According to various embodiments, the harvesting energy 403 unit may be a bio-inspired hair cell similar to the one shown in FIG. 2D, or may be based on piezoelectric circuit such as the one shown in FIG. 2E.

In FIG. 2D, which is taken from a publication "Asadnia et al., From Biological Cilia to Artificial Flow Sensors, SciRep (2016)", two micrographs (a) and (c), as well as two schematic views (b) and (d) are shown to illustrate the architecture and principles of mechano-transduction of ciliary bundles in nature. Part (a) of FIG. 2D shows a morphology of saccular hair bundles in the bullfrog. In this organ, each bundle consists of approximately 60 stereocilia arranged into 8 rows with heights varying from 4 to 8 µm (scale bar is 3 µm). Part (b) of FIG. 2D shows a schematic illustrating the deflection of a column of stereocilia during stimulation. A deflection of the hair bundle causes a shear between successive rows of stereocilia causing the tip links to tighten. Part (c) of FIG. 2D shows a transmission electron micrograph showing the tip link between two adjacent stereocilia (scale bar is 1 µm), while part (d) of FIG. 2D shows how a tension induced in the tip link can open ion channels.

FIG. 2E, which is taken from a publication "*MEMS Based Broadband Piezoelectric Ultrasonic Energy Harvester (PUSH) for Enabling Self-Powered Implantable Biomedical Devices*" (Scientific Reports volume 6, Article number: 24946 (2016)), shows in part (a) a micrograph image (a bird view) of a piezoelectric ultrasonic energy harvester, and shows in part (b) a cross-sectional view (SEM image) of the piezoelectric ultrasonic energy harvester. In this example, the energy harvester comprises of a piezoelectric PZT layer embedded between two platin electrodes, which are deposited on a Si/SiO2 substrate.

Figure 2F:
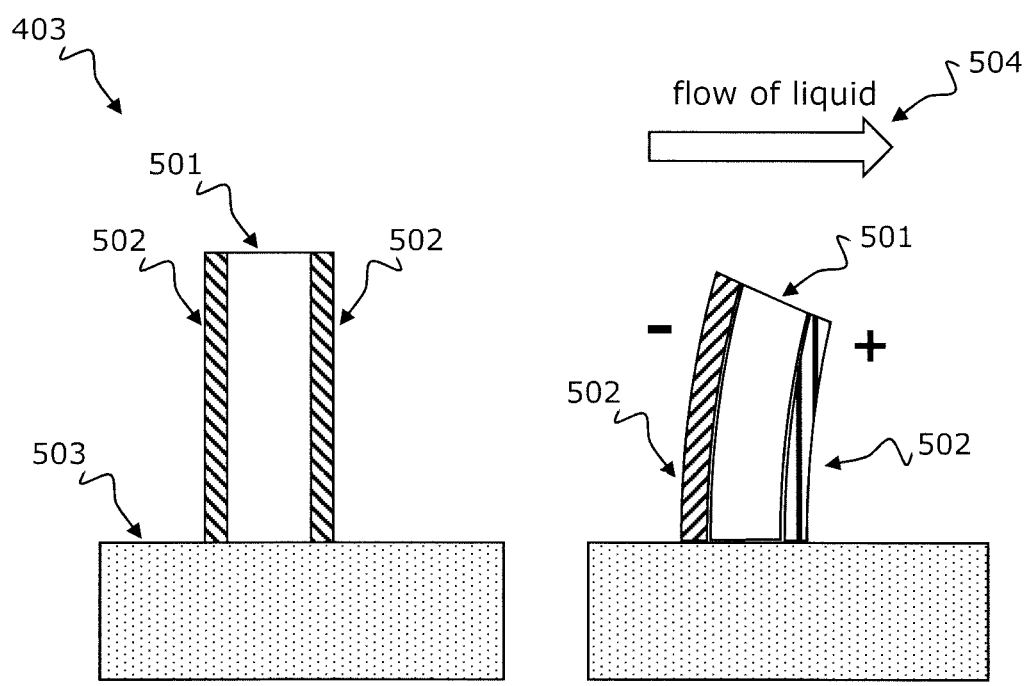
FIG. 2F illustrates a schematic graph for illustrating the generation of an electrical potential in an energy harvesting unit according to an embodiment of the invention.

FIG. 2F shows in the left part of the FIG. 2F an example according to various embodiments, which is comprises a PZT layer 501 embedded between two metal electrodes 502, which is arranged on a base portion 503. The metal electrodes 502 are each connected to an electric circuit (not shown). The arrangement corresponds to an example of an energy harvesting 403, which can be introduced into the cochlea 105 of the user.

In case of a flow of liquid 504 inside the cochlea 105 (in FIG. 2F, a flow of liquid to the right), the liquid in will exhibit a force bending the energy harvesting unit to the right which may generate e.g. a positive voltage (sign "+") on the right electrode 502 and a negative voltage (sign "−") on the left electrode 502. In case the liquid flows to the left side, the voltages will be reversed. The voltages can be used by the electric circuit to generate a supply voltage as an output from the energy harvesting unit 403.

In other words, under the influence of vibrations of the surrounding liquid, electrical potentials are generated on the metal electrodes 502 by the piezoelectric effect in the PZT layer 501. The metal electrodes 502 can be made from platinum, gold and the like. In this way, electrical energy may be harvested by the energy harvesting unit.

In other words, according to various embodiments the energy harvesting apparatus may be based on an actuator made from a piezoelectric material.

Figure 3:
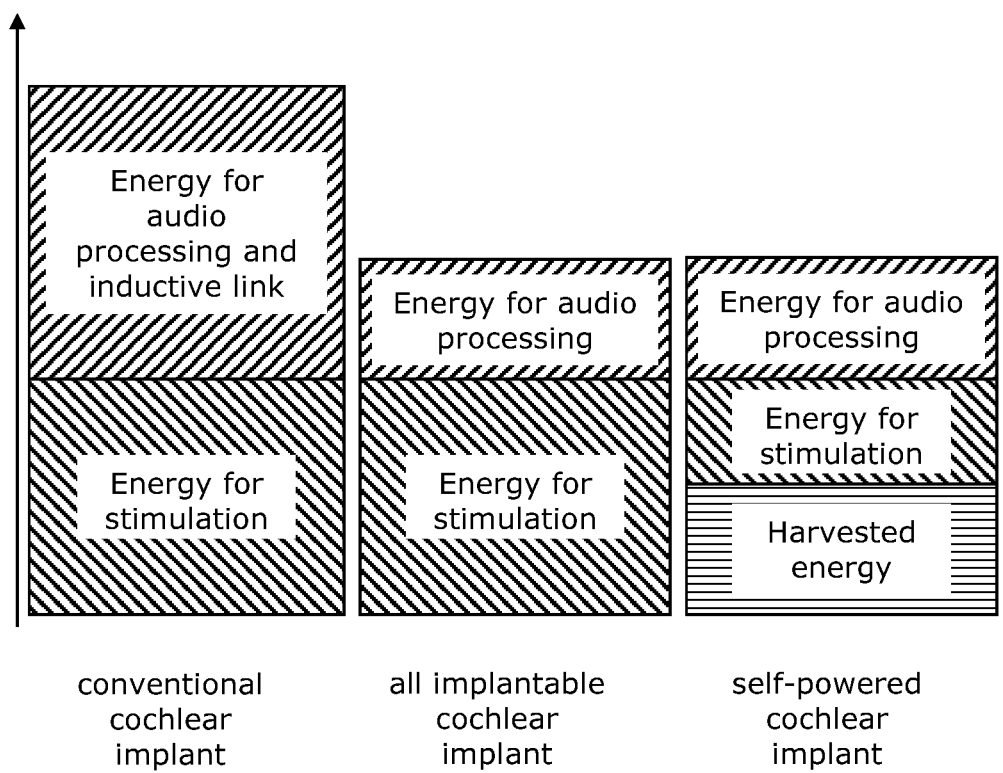
FIG. 3 shows a diagram to illustrate the effect of an energy harvesting apparatus according to an embodiment of the invention.

FIG. 3 is a graph for illustrating the effect of the cochlear implant comprising the energy harvesting apparatus 310. It is noted that an extension along the vertical axis corresponds to an overall energy consumption of the cochlear implant.

On the left side in FIG. 3, the energy consumption of a conventional cochlear implant is depicted. The overall energy consumption consists of an energy required for the stimulation of the cochlea of the user and an energy required for the processing of the audio signals and an energy lost due to the inductive link.

Using an all implantable cochlear implant having a battery, the energy lost due to the inductive link can be reduced or completely avoided, so that the overall energy consumption can be reduced (middle part of FIG. 3).

Using a self-powered cochlear implant according to various embodiments, which comprises an energy harvesting apparatus 310 a part of the energy required for the stimulation of the cochlea can be taken from the energy harvesting apparatus 310, so that the energy, that needs to be provided from an additional battery or by the inductive link can be even further reduced. By the reduction of the energy required to operate the system, for example the size of an additional implantable battery can be reduced.

Figure 4:
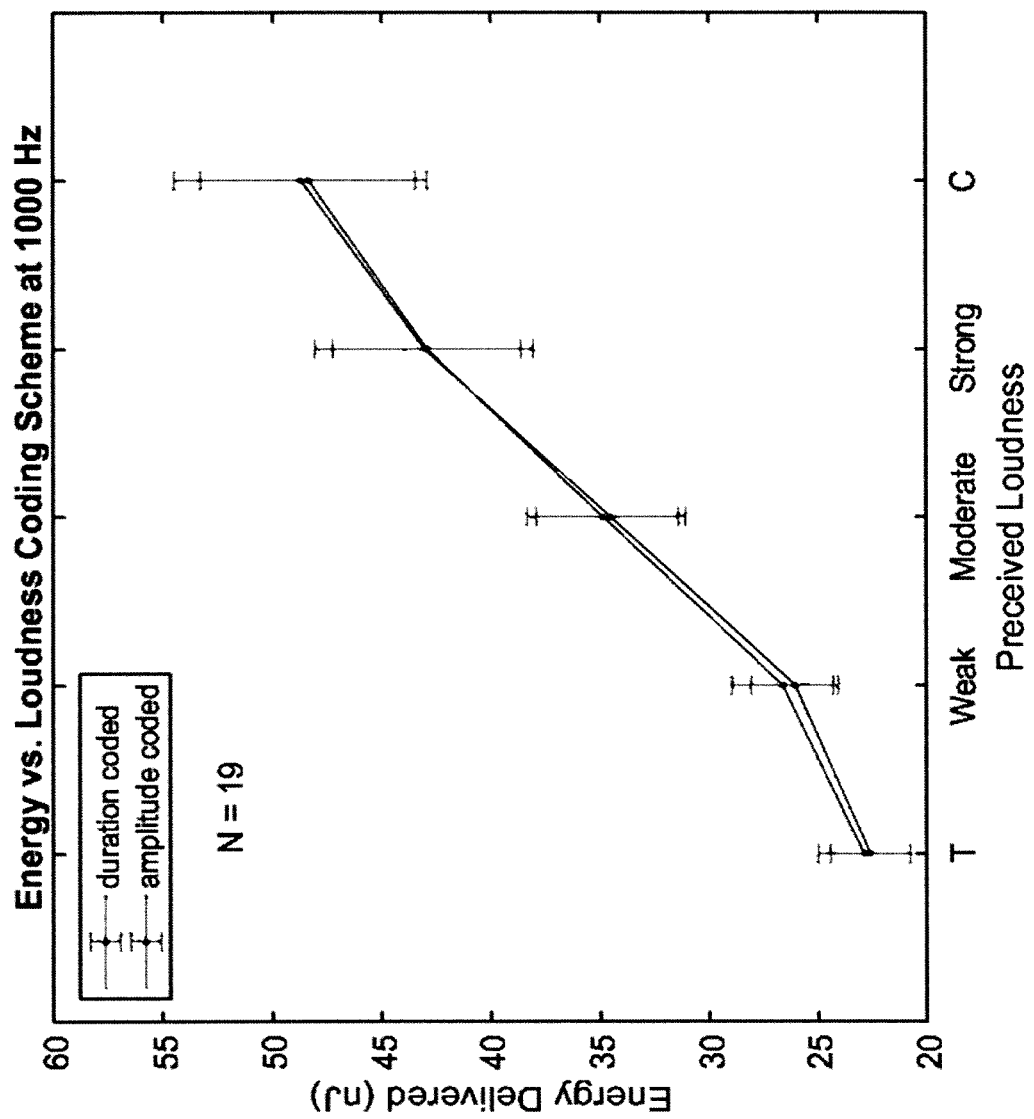
FIG. 4 shows a graph for illustrating a relation between a delivered energy and a perceived loudness.

FIG. 4 shows a plot of the energy requirements for stimulation by one electrode of the electrode array according to various embodiments. The horizontal axis indicates the perceived loudness while the vertical axis in FIG. 4 indicates the energy delivered in units of nJ. The graph shows an average for 19 users of the energy requirement on an electrode corresponding to 1000 Hz with a fixed assumed resistance value of 1000 Ohm. The stimulation rate was set to 500 Hz. The amount of energy that is required to provide from the stimulation unit is for example in case of a moderate perceived loudness about 35 nJ every 2 ms. Two curves are shown in FIG. 4, one for a duration coded signal, and one for an amplitude coded signal, which however fall together within the error margins. This required energy can be provided in part or in full by the harvested energy harvested by the energy harvesting unit.

Therefore, roughly 25 nJ per one ms need to be harvested which equals to 25 uW of power. This energy must be harvested from the human body, which restricts the minimum size of the energy harvesting apparatus.

Taking e.g. the tympanic membrane as an energy source, the amount of mechanical vibrational energy present at the typanic membrane and available for harvesting can be estimated as follows:

The energy E of a mechanical system having a moving mass m can be captured at its maximum kinetic point at the maximum velocity v_max, as $E=m/2 \cdot v^2\_max$. The typanum has been measured to move by 0.2 mm/s/Pa (Rosowsky et al. 2012). Since a sound pressure of 1 Pa=94 dB sound pressure level (SPL) (which is quite loud), 0.01 mm/s may be assumed as v_max at 68 dB SPL. The moving mass of the tympanic membrane is roughly 20 mg. So the available energy at the input can be calculated to be:

$$E=20E\text{-}6(\text{kg}) \cdot 0.01E\text{-}3(\text{m/s})^2 = 2E\text{-}15 \text{ J or } 2E\text{-}6 \text{ nJ per cycle.}$$

Since a total of 25 nJ needs to be captured at each cycle for 1000 Hz input, additional energy is still required to read input via the coil of the cochlear implant. It is noted that the process of harvesting this vibration will further dampen the mechanical vibration.

According to various embodiments, the cochlear implant device may in addition comprise an energy storage apparatus connected to the energy harvesting apparatus and configured to be charged by the energy harvesting apparatus. For example, the self powered cell may comprise a small capacitor to store electrical energy.

Even further, according to various embodiments, the cochlear implant device or the energy harvesting unit may additionally comprise a rectifying means for rectifying the voltage generated by the energy harvesting unit for charging of the energy storage apparatus.

Figure 6:
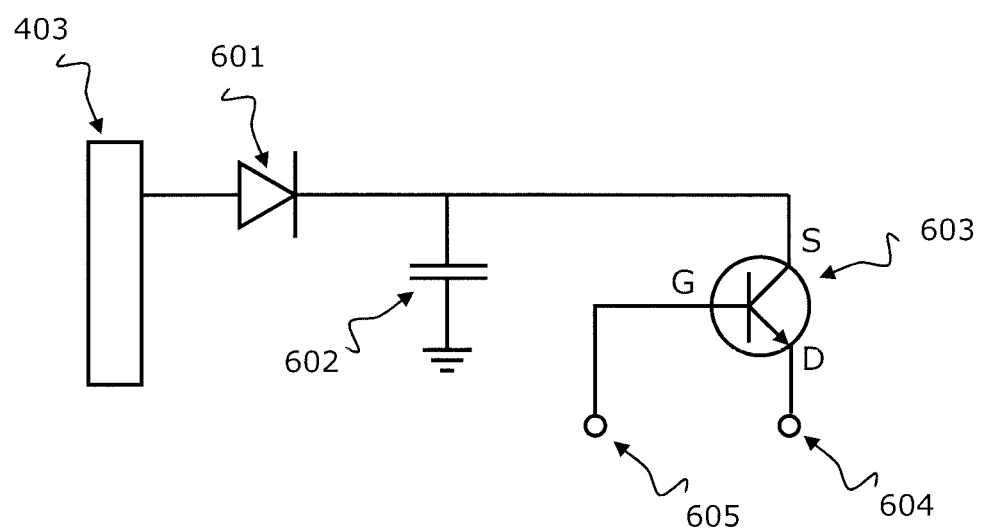
FIG. 6 illustrates a circuit diagram for use with an energy harvester.

FIG. 6 illustrates a respective example according to various embodiments: an energy harvesting unit 403 is connected to a rectifier 601 (e.g., a diode) which rectifies an oscillating voltage coming from the energy harvesting unit 403 into a direct-current voltage. The direct current voltage can be stored in the energy storage apparatus 602 (e.g., a capacitor), while an additional switching means 603 is provided to switch the direct current voltage rectified by the rectifier 601 according to and control signal from the stimulation unit 222, which is input through the control signal terminal 605. The output of the switching means 603 is guided to the electrode through the electrode terminal 604.

In other words, according to various embodiments, the energy storage apparatus 602 may comprise a capacitor connected to the energy harvesting unit 403 via the rectifying means 601 and connected to the switching means 603.

According to various embodiments, the switching means 603 may be any of a transistor, a MOSFET, or the like. The energy storage apparatus 602 can be a capacitor, a super capacitor, or the like.

According to various embodiments, the switching means 603 may be a single transistor solution or a single MOSFET solution, so that the pulse shape of a specific signal may be difficult to control. This is because the pulse shape may be influenced by the charge state of the capacitor. That is because if energy is stored as a voltage in a capacitor, the voltage may decay exponentially as its power is used, and may increase exponentially as it is harvested (charged). However, it is possible to compensate these variations by using a control signal, which is applied to the gate of the transistor or MOSFET. To further control the energy delivery during stimulation, additional non-passive electronic components may be used to shape the electrical pulses.

Furthermore, according to various embodiments, it is possible to monitor the charge state of the capacitor. Such monitoring may be used to adjust the duration of the signal, in order to produce a certain loudness.

In addition, according to various embodiments, the energy storage apparatus 602 may be configured to be charged additionally by energy received by the inductive antenna 103, and the inductive antenna 103 may further be configured to receive energy for supplying energy to the energy storage apparatus 602.

According to various embodiments, the energy coming from the energy harvesting apparatus may be stored in a capacitor, and the signal coming from the stimulation unit and entering in the "self-powered cell" via the control signal terminal 605 is working like a trigger to control the stimulation delivered to the cochlea 105.

That is, according to various embodiments, each electrode of the electrode array 104 may be provided with a switching means 603 configured to apply the energy stored in the energy storage apparatus 602 to the respective electrode in accordance with the received electrical stimulation signals from the stimulation unit 222.

Furthermore, according to various embodiments, the switching means may be configured to provide an electrical amplification of the electrical stimulation signals.

Additionally, according to various embodiments, the cochlear implant described before may provide a direct input for harvested energy coming from self powered cells 402 by a an additional electrical track in the electrode array. Hence, according to various embodiments, the self-powered cells may be connected to the stimulator unit, so that the electrode array becomes a "bi-directional array".

According to the discussion above, according to various embodiments, the amount of energy that is required to provide from the stimulation unit is for example in case of a moderate perceived loudness is about 35 nJ. Hence, a capacitor 602 being capable of storing 50 nJ may be used.

The volumetric storage requirements for holding 50 nJ can be calculated using a formula for the energy E stored in a capacitor having capacitance C charged with voltage V, which is $E=\frac{1}{2} C*V^2$. Assuming and operation voltage of 1V, this results in a required capacitance C=100 nF.

As an example, a commercial capacitor having a capacitance of 100 nF of the so-called "0201" size may be used.

Figure 5:
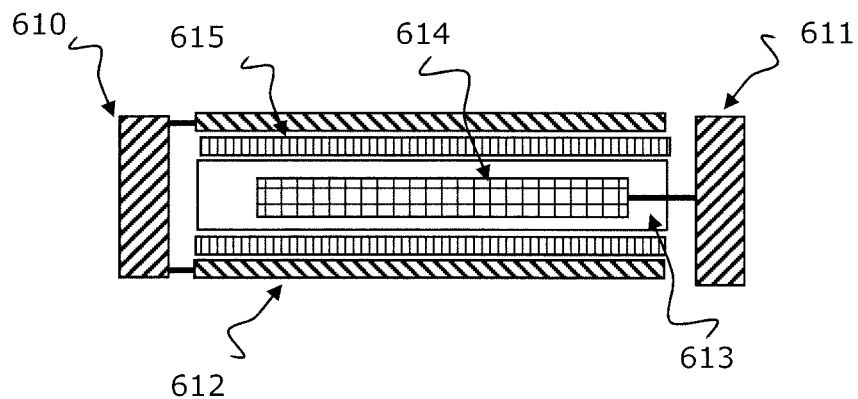
FIG. 5 illustrates a schematic setup of a capacitor.

However, a capacitor can be built using the design shown in FIG. 5. The capacitor comprises two electrodes 610, 611, an older charge storage plate 612, an inner charge storage plate 613, a wire layer 614 and dielectric layers 615.

As for the dielectric layer, different dielectrics (for example, X6S, Y5V, and X5R) are commercially available having different properties. The electrodes 610, 611 as well as the wire layer 614 may be made from a metal having a good electrical conductivity, such as aluminum, copper, silver of gold. It may be required to use biocompatible metals, such as platinum or the like.

Using such a design as depicted in FIG. 5, a total energy density at 1V operating voltage may be 100nJ/0.0594 mm^3. Furthermore, the energy storage apparatus 602 may be directly integrated into the multichannel electrode array and may be made from flexible materials.

A cochlear implant typically includes i) an external part for picking up and processing sound from the environment, and for determining sequences of pulses for stimulation of the electrodes in dependence on the current input sound, ii) a (typically wireless, e.g. inductive) communication link for simultaneously transmitting information about the stimulation sequences and for transferring energy to iii) an implanted part allowing the stimulation to be generated and applied to a number of electrodes, which are implantable in different locations of the cochlea allowing a stimulation of different frequencies of the audible range. Such systems are e.g. described in U.S. Pat. No. 4,207,441 and in U.S. Pat. No. 4,532,930.

In an aspect, the hearing device comprises multi-electrode array e.g. in the form of a carrier comprising a multitude of electrodes adapted for being located in the cochlea in proximity of an auditory nerve of the user. The carrier is preferably made of a flexible material to allow proper positioning of the electrodes in the cochlea such that the electrodes may be inserted in cochlea of a recipient. Preferably, the individual electrodes are spatially distributed along the length of the carrier to provide a corresponding spatial distribution along the cochlear nerve in cochlea when the carrier is inserted in cochlea.

In an aspect, the functions may be stored on or encoded as one or more instructions or code on a tangible computer-readable medium. The computer readable medium includes computer storage media adapted to store a computer program comprising program codes, which when run on a processing system causes the data processing system to perform at least some (such as a majority or all) of the steps of the method described above, in the and in the claims.

By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media. In addition to being stored on a tangible medium, the computer program can also be transmitted via a transmission medium such as a wired or wireless link or a network, e.g. the Internet, and loaded into a data processing system for being executed at a location different from that of the tangible medium.

For example, the signal conditioning method which may be performed on the signal processing unit in the cochlear implant may be provided on a computer-readable medium.

In an aspect, a data processing system comprising a processor adapted to execute the computer program for causing the processor to perform at least some (such as a majority or all) of the steps of the method described above and in the claims.

It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

REFERENCE SIGNS 101 sound processor
102 external antenna
103 implanted coil of the cochlear implant
104 electrode array
105 cochlea
106 auditory nerve
107 acoustic sound
202 microphone
203 signal processing unit
204 battery
210 inductive field
220 cochlear implant
222 stimulation unit
310 energy harvesting apparatus
401 multi-channel electrode array
402 self-powered cell
403 energy harvesting unit
404 signal conditioner
501 PZT layer
502 metal electrodes
503 base portion
504 flow of liquid
601 rectifier
602 energy storage apparatus
603 switching means
604 electrode terminal
605 control signal terminal
610 electrode
611 electrode
612 outer charge storage plate
613 inner charge storage plate
614 wire layer
615 dielectric layer

The invention claimed is:

1. A cochlear implant device for improving or augmenting the hearing capability of a user of the cochlear implant device, comprising:
    an inductive antenna configured to receive energy to operate the cochlear implant and to receive signals for a stimulation of a cochlea via an electrode array comprising a plurality of electrodes, and wherein the received signals include audio;
    a stimulation unit configured to process the received signals received by the inductive antenna to be usable for the electrodes of the electrode array, and the electrode array is configured to apply the received signals processed by the stimulation unit to the cochlea for the stimulation thereof; and
    an energy harvesting apparatus connected to the electrode array, wherein the electrode array and the energy harvesting apparatus are inserted into the scala tympani of the cochlea so that a piezoelectric actuator of the energy harvesting apparatus is inserted into a flow path of organic cochlear liquid, and wherein the energy harvesting apparatus is configured to harvest energy generated as a result of the piezoelectric actuator being bent by movement of the cochlear liquid, the energy harvesting apparatus being configured to provide the harvested energy to the stimulation unit or the electrode array, respectively.

2. The device according to claim 1, wherein
the energy harvesting apparatus is attached and electrically connected to the electrode array.

3. The device according to claim 1, wherein
the piezoelectric actuator of the energy harvesting apparatus is configured as part of a harvesting unit having a hair shape configured to generate an electrical potential under the influence of movement of the cochlear liquid.

4. The device according claim 1,
further comprising an energy storage apparatus connected to the energy harvesting apparatus and configured to be charged by the energy harvesting apparatus.

5. The device according to claim 4, wherein
the energy harvesting apparatus additionally comprises a rectifying means for rectifying the voltage generated by the energy harvesting apparatus for charging of the energy storage apparatus.

6. The device according to claim 4, wherein
the energy storage apparatus is further configured to be additionally charged by energy received by the inductive antenna, and the inductive antenna is further configured to receive energy for supplying energy to the energy storage apparatus.

7. The device according to claim 4, wherein
each electrode of the electrode array is provided with a switching means configured to apply the energy stored in the energy storage apparatus to the respective electrode in accordance with the received electrical stimulation signals from the stimulation unit.

8. The device according to claim 7, wherein
the switching means is configured to provide an electrical amplification of the electrical stimulation signals.

9. The device according to claim 7, wherein
the energy storage apparatus comprises a capacitor connected to the energy harvesting apparatus and connected to the switching means.

10. The hearing device according to claim 1, wherein
the inductive antenna is further configured to transmit information relating to the cochlear implant.

11. The device according claim 2,
further comprising an energy storage apparatus connected to the energy harvesting apparatus and configured to be charged by the energy harvesting apparatus.

* * * * *